United States Patent [19]

Reiter et al.

[11] Patent Number: 5,092,769
[45] Date of Patent: Mar. 3, 1992

[54] TENSIONING HANDLE FOR ROOT-CANALLING INSTRUMENTS

[75] Inventors: Johann Reiter; Karl Schottenheim, both of München, Fed. Rep. of Germany

[73] Assignee: Vereinigte Dentalwerke Antaeos-Beutelrock-Zipperer Zdarsky Ehrler GmbH & Co. KG, München, Fed. Rep. of Germany

[21] Appl. No.: 605,913

[22] Filed: Oct. 30, 1990

[30] Foreign Application Priority Data

Oct. 31, 1989 [DE] Fed. Rep. of Germany ....... 3936211

[51] Int. Cl.⁵ .......................... A61C 5/02; A61C 3/00
[52] U.S. Cl. ..................................... 433/102; 433/147
[58] Field of Search ................ 433/102, 141, 146, 147

[56] References Cited

U.S. PATENT DOCUMENTS 4,251,214 2/1981 Schnall ................................. 433/147
4,582,489 4/1986 Listl ..................................... 433/102

*Primary Examiner*—John J. Wilson
*Assistant Examiner*—Cindy A. Cherichetti
*Attorney, Agent, or Firm*—Max Fogiel

[57] ABSTRACT

Tensioning handle for a root-canalling instrument and comprising a grip (1) with an outside-threaded shank (2) at one end, an inside-threaded cap (3) that screws onto the shank, a bore (4) that extends axially through the shank and the cap, and a tensioner that surrounds a tool inserted in the bore and tightens around the shaft of the tool when the cap is screwed tight, characterized in that the tensioner comprises sleeves (10) that loosely surround the shaft (5) of the tool (6) and have opposing sloping surfaces (15 & 16) that displace them laterally when the cap is screwed on.

8 Claims, 1 Drawing Sheet

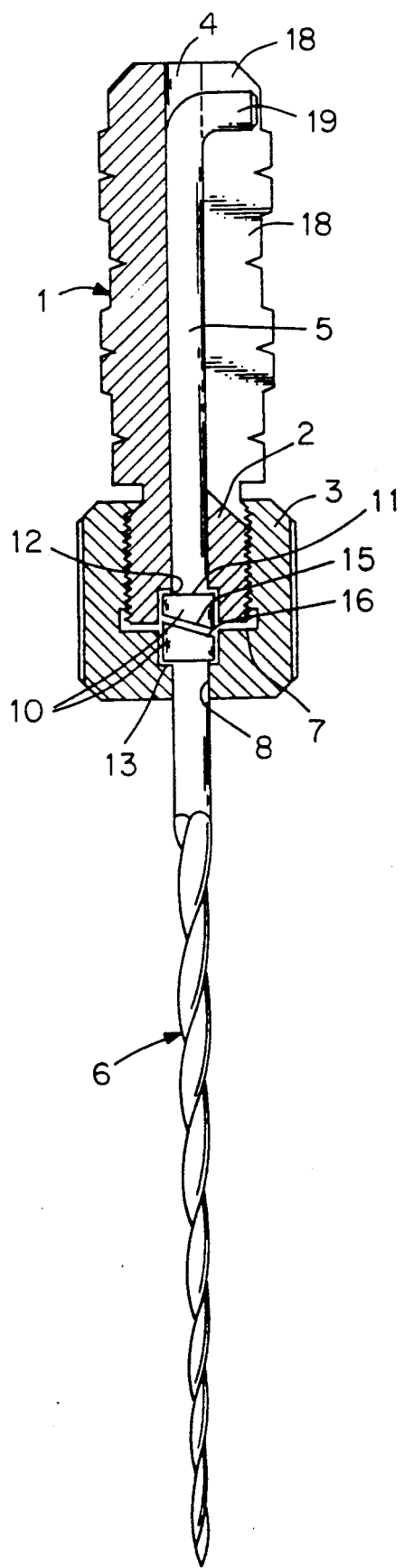

1

TENSIONING HANDLE FOR ROOT-CANALLING INSTRUMENTS

BACKGROUND OF THE INVENTION

The invention concerns a tensioning handle for a root-canalling instrument in accordance with the preamble of the base claim.

A tensioning handle of this type is known from German Patent 3 403 654 (U.S. Pat. No. 4,582,489). It has a grip with an outside-threaded shank at one end. An inside-threaded cap screws onto the shank. A bore extends axially through the grip, shank, and cap. Between the shank and the cap is a tensioner. A tool is inserted into the bore, and the threaded components are screwed tight, forcing the tensioner against the shaft of the tool. The tensioner is a conventional helical spring that loosely surrounds the tool shaft opposite the threads, with its ends accommodated in depressions in the threaded components. When the cap is screwed onto the shank of the grip, the spring is entrained at its ends and rotated in. Its coils wrap tight around the tool shaft and secure it. The spring must be manufactured and its ends inserted into the depressions that accommodate them with particular care to ensure reliable tension and easy employment of the cap. A handle of this type is accordingly expensive. Another tensioning handle of a similar design is known from German Patent 2 703 637. It employs a tensioner in the form of a washer instead of a spring. A bore that accommodates the shaft of the tool extends at an angle through the disk but in alignment with the bore through the threaded components. When the threaded components are screwed together, the disk is shifted out of its rest position, with its bore at an angle to that through the threaded components, and compressed. Here again, the manufacturing process is expensive because even slight deviations in the tolerance of such a small component can impair is effectiveness.

SUMMARY OF THE INVENTION

The object of the invention is to provide a tensioning handle for a root-canalling instrument with a tensioner that is easy and hence inexpensive to manufacture, while effectively securing the tool.

This object is attained in accordance with the invention in a tensioning handle of the aforesaid type by the characteristics recited in the body of base claim.

Advantageous advanced embodiments of the invention are recited in the dependent claims.

The sleeves that constitute the tensioner can be easily and inexpensively cut to size from commercially available structural section or tubing. No special demands are made as to the properties of its sloping surfaces. Since the two sleeves that constitute each tensioner match, production can be limited to one size. The sleeves are also easy to insert between the threaded components with their sloping surfaces facing each other. Since the sloping surfaces can displace to a considerable extent when the threaded components are screwed together, the sleeves will be forced tight against the shaft of the tool even in the event of manufacturing tolerances. The resulting tightness will be retained until the cap is unscrewed again. The comparatively extensive contact surfaces inside the tensioner will avoid damage in the form of scratches on the shaft of the tool.

BRIEF DESCRIPTION OF THE DRAWINGS

One embodiment of the invention will now be specified with reference to the drawing, which is an axial section.

BRIEF DESCRIPTION OF THE PREFERRED EMBODIMENTS

The tensioning handle consists of a grip 1 with an outside-threaded shank 2 at one end. An inside-threaded cap 3 screws onto the shank. A bore 4 extends axially through the grip and the cap. The shaft 5 of a root-canalling tool 6 is inserted loosely into the bore. Bore 4 aligns with another bore 8 through the top 7 of cap 3. Bore 8 can be slightly wider than bore 4. The inserted tool is secured in its desired operating position by a tensioner in the form of two sleeves 10 accommodated between 2 and cap 3. The bores 11 that extend through sleeves 10 are slightly wider than the shaft, which they accordingly surround somewhat loosely. The sleeves themselves are secured in the shank and cap in a practical way by two matching bores 12 and 13 that are again slightly wider and accommodate the ends of the sleeves. Although the depth of the accommodation bores can vary, they must not be large enough to allow the faces of shank 2 and cap 3 to come into contact when the tool is tensioned in. It is of advantage for accommodation bores 12 and 13 to be deep enough to securely seat the sleeves even when no tool is inserted, so that they will not tilt out of alignment. To ensure that the sleeves will secure the tool in position, they are provided with sloping surfaces 15 and 16 that face each other when the sleeves are in their bores. It is practical for these surfaces to slope at an angle of 45° to the bores.

To position a tool 6 inserted in the handle to a desired length, it is inserted to the desired depth with cap 3 still loose. The cap is then tightened, forcing the sloping surfaces 15 and 16 of sleeves 10 together and laterally opposing the sleeves. The walls of the bores through the sleeves are accordingly forced against the shaft of the tool, tensioning it in position. Since the sleeves react very sensitively, even a slight force on the part of the cap as it is being screwed on will provide sufficient tension, which can also easily be eliminated simply by unscrewing the cap slightly.

The handle may have, as does the illustrated example, a longitudinal slot 18 for inserting a bent section 19 of the tool into in order to keep it from rotating in the bore and to facilitate adjusting its length. Other types of handle, however, are just as conceivable. The tensioning procedure in accordance with the invention is also not restricted to measuring handles for manual instruments, but is also applicable to straight or angled inserts in manually operated or motorized equipment. The components can be made of plastic, metal, or both. The handle can be knurled or ridged to facilitate manipulation.

We claim:

1. A tensioning handle for a root canal instrument comprising: a grip having an end with an outside-threaded shank; a cap having an inside thread for screwing onto said shank; said shank and said cap having a bore extending axially through said shank and cap for holding a tool with shaft insertable in said bore; tensioning means surrounding an inserted tool and tightening around the shaft of the tool when said cap is screwed tight on said shank; said tensioning means comprising sleeves surrounding loosely said shaft of said tool and having opposing sloping surfaces for displacing said sleeves laterally when said cap is screwed on; said sleeves having cylindrical axes; said sloping surfaces being inclined relative to said cylindrical axes.

2. A tensioning handle as defined in claim 1, wherein said shank and said cap have cylindrical bores for holding said sleeves.

3. A tensioning handle as defined in claim 2, wherein said cylindrical bores are substantially larger in diameter than said sleeves.

4. A tensioning handle for a root canal instrument comprising: a grip having an end with an outside-threaded shank; a cap having an inside thread for screwing onto said shank; said shank and said cap having a bore extending axially through said shank and cap for holding a tool with a shaft insertable in said bore; tensioning means surrounding an inserted tool and tightening around the shaft of the tool when said cap is screwed tight on said shank; said tensioning means comprising sleeves surrounding loosely said shaft of said tool and having opposing sloping surfaces for displacing said sleeves laterally when said cap is screwed on; said opposing sloping surfaces being inclined at an angle of substantially 45° to axes of said sleeves.

5. A tensioning handle for a root canal instrument comprising: a grip having an end with an outside-threaded shank; a cap having an inside thread for screwing onto said shank; said shank and said cap having a bore extending axially through said shank and cap for holding a tool with a shaft insertable in said bore; tensioning means surrounding an inserted tool and tightening around the shaft of the tool when said cap is screwed tight on said shank; said tensioning means comprising sleeves surrounding loosely said shaft of said tool and having opposing sloping surfaces for displacing said sleeves laterally when said cap is screwed on; said sleeves having first bores coaxial with said shaft, said first bores having a diameter substantially larger than the diameter of said shaft; said shank and said cap having second bores for receiving said sleeves, said second bores being substantially larger in diameter than said sleeves to allow relative displacement of said sleeves in radial direction, said sloping surfaces being inclined relative to axes of said sleeves and said shaft, said sleeves rotating in opposite directions relative to each other during screwing of said cap on said shaft due to friction between said second bores and said sleeves, relative rotation of said sleeves pressing said sloping surfaces against each other for displacing said sleeves relative to each other and thereby abutting a part of an inner surface of said second bores against said shaft to secure said shaft through surface pressure on said shaft.

6. A tensioning handle as defined in claim 5, wherein said shank and said cap have cylindrical bores for holding said sleeves.

7. A tensioning handle as defined in claim 6, wherein said cylindrical bores are substantially larger in diameter than said sleeves.

8. A tensioning handle as defined in claim 5, wherein said opposing sloping surfaces are inclined at an angle of substantially 45° to axes of said sleeves.

* * * * *